United States Patent
Barry

[11] 4,020,679
[45] May 3, 1977

[54] SLED FOR ULTRASONIC NDT SYSTEM

[75] Inventor: Peter S. Barry, Roxbury, Conn.

[73] Assignee: Automation Industries, Inc., Los Angeles, Calif.

[22] Filed: Aug. 13, 1975

[21] Appl. No.: 604,268

[52] U.S. Cl. .................. 73/67.8 S; 73/71.5 US; 310/8.7

[51] Int. Cl.² .................................. G01N 29/04

[58] Field of Search ............. 73/67.5 R, 67.6, 67.7, 73/67.8 R, 67.8 S, 67.9, 71.5 US; 310/8.3, 8.7

[56] References Cited
UNITED STATES PATENTS

| | | | |
|---|---|---|---|
| 2,505,867 | 5/1950 | Meunier | 73/67.6 |
| 2,545,309 | 3/1951 | Roberts | 73/67.6 |
| 3,242,723 | 3/1966 | Evans | 73/71.5 US |
| 3,602,036 | 8/1969 | Peterson | 73/67.8 R |
| 3,631,714 | 1/1972 | Cressman et al. | 73/71.5 US |
| 3,798,961 | 3/1974 | Flambard et al. | 73/71.5 US |
| 3,821,834 | 7/1974 | McElroy | 310/8.3 |
| 3,832,889 | 9/1974 | Bauer | 73/71.5 US |
| 3,847,016 | 11/1974 | Ziedonis | 73/71.5 US |
| 3,913,386 | 10/1975 | Saglio | 73/67.5 R |

Primary Examiner—Richard C. Queisser
Assistant Examiner—John P. Beauchamp
Attorney, Agent, or Firm—Thomas L. Flattery

[57] ABSTRACT

An ultrasonic nondestructive testing system and a "sled" for use in such a system are provided for nondestructively inspecting a workpiece. The "sled" includes an ultrasonic search unit effective to radiate or transmit ultrasonic energy in response to a driving signal and to receive ultrasonic energy and produce a received signal corresponding to the incident ultrasonic energy. The sled includes a sealed chamber filled with a liquid couplant. A resilient, elastomeric diaphragm forms one side of the chamber and is adapted to slide along the surface of the workpiece. An ultrasonic search unit projects into the chamber so as to be acoustically coupled to the diaphragm. In addition, an elastomeric member having a high acoustical attenuation and an acoustical impedance corresponding to that of the liquid couplant is provided inside of the chamber for absorbing spurious ultrasonic energy.

7 Claims, 6 Drawing Figures

SLED FOR ULTRASONIC NDT SYSTEM

In a typical ultrasonic nondestructive testing system, a search unit is provided for transmitting ultrasonic energy into a workpiece in response to an electrical driving signal and for producing electrical received signals corresponding to the ultrasonic energy received by the search unit from the workpiece.

In a so-called pulse-echo system, the search unit is adapted to transmit bursts or pulses of ultrasonic energy in response to a repetitively occurring driving signal whereby the pulses of ultrasonic energy are propagated into the workpiece. Echoes of the ultrasonic energy are reflected back to the search unit from any discontinuities such as the front and rear surfaces of the workpiece, and any cracks, voids, inclusions, etc., which may be inside of the workpiece. The search unit in turn generates electrical received signals corresponding to the echoes received by the search unit. By measuring the amplitude and time delay of the received signals, it is possible to determine the size and position of the discontinuity.

To obtain an accurate measurement of the size, position, etc., of a discontinuity, it is necessary to accurately measure the amplitude and time, etc., of the received signal generated by the search unit. To accomplish this objective, it is highly desirable the pulses of ultrasonic energy transmitted by the search unit correspond closely to the electrical signals driving the search unit. Conversely, the received signals generated by the search unit should correspond closely to the ultrasonic energy incident on the search unit. It is also essential that the search unit not create any spurious signals which might tend to mask a valid signal or be confused with a valid signal.

A search unit intended for use in an ultrasonic nondestructive testing system usually employs a piezoelectric element or crystal to produce the ultrasonic energy in response to the driving signal and to conversely generate an electrical signal in response to the incident ultrasonic energy. Since the ultrasonic energy is normally highly attenuated by air, it is necessary to provide some form of acoustical coupling between the search unit and the workpiece. Various types of acoustical coupling are available for this purpose. In the so-called contact type of testing, the face of the search unit is placed in direct contact with the surface of the workpiece. A film or puddle of liquid couplant such as water or glycerin may be provided to enhance the effectiveness of the coupling.

In addition, a coupling member or shoe may be provided on the face of the search unit. This shoe is normally a rigid material such as a plastic and rides or slides along the surface of the workpiece. This shoe is effective to act as a coupling member and as a wear receiving member. It is frequently desirable for the ultrasonic energy to enter the workpiece at some predetermined oblique angle. In this event the shoe can be inclined or wedged shaped whereby the search unit is oriented at the oblique angle to the workpiece.

Although the use of plastic shoes, wedges, etc., have been extremely useful, they do have limitations and they do present problems. Because of the acoustical properties of the material in the shoes, there is frequently a significant amount of attenuation of the ultrasonic energy. Also, the resolution, particularly near the interface between the shoe and the workpiece (i.e., near surface defects) tends to be very poor. This is particularly true where the surface of the workpiece is not flat, for example, it contains even minor undulations and irregularities. It has further been found that a plastic shoe tends to wear relatively rapidly as it is worked over the surface of the workpiece. This wearing results in an irregular surface which degrades the coupling. It can also result in a change in the angle of incidence which further degrades the resolution and accuracy of the search unit.

It has also been found that when a burst of ultrasonic energy is transmitted into the shoe, at least a portion of the energy tends to reflect around the inside of the shoe. These multiple reflections or reverberations are received by the search unit whereby large amounts of spurious signals are produced. This can be particularly troublesome when the angle of incidence is small.

SUMMARY

The present invention provides means for overcoming the foregoing difficulties. More particularly, the present invention provides a "sled" adapted to slide or ride along the surface of the workpiece. A search unit is mounted in the "sled" for transmitting ultrasonic energy in response to electrical driving signals and also to receive ultrasonic energy and produce corresponding received electrical signals.

The sled includes an enlarged cavity or chamber therein which is filled with a liquid couplant effective to transmit ultrasonic energy therethrough. An elastomeric membrane or diaphragm forms one side of the cavity. This membrane or diaphragm forms a flexible face suitable for sliding along the surface of the workpiece. This flexible face has the ability to closely follow any irregularities in the surface of the workpiece. In addition, one or more pieces of an elastomeric material are disposed inside of the cavity in intimate contact with the liquid couplant. This material has an acoustical impedance closely matching that of the liquid couplant whereby there will be little or no spurious energy reflected from the interface of the elastomer back into the liquid couplant. In addition, the elastomer has a high attenuation of ultrasonic energy whereby the energy is absorbed and dissipated inside of the elastomer.

DRAWINGS

DESCRIPTION

Figure 1:
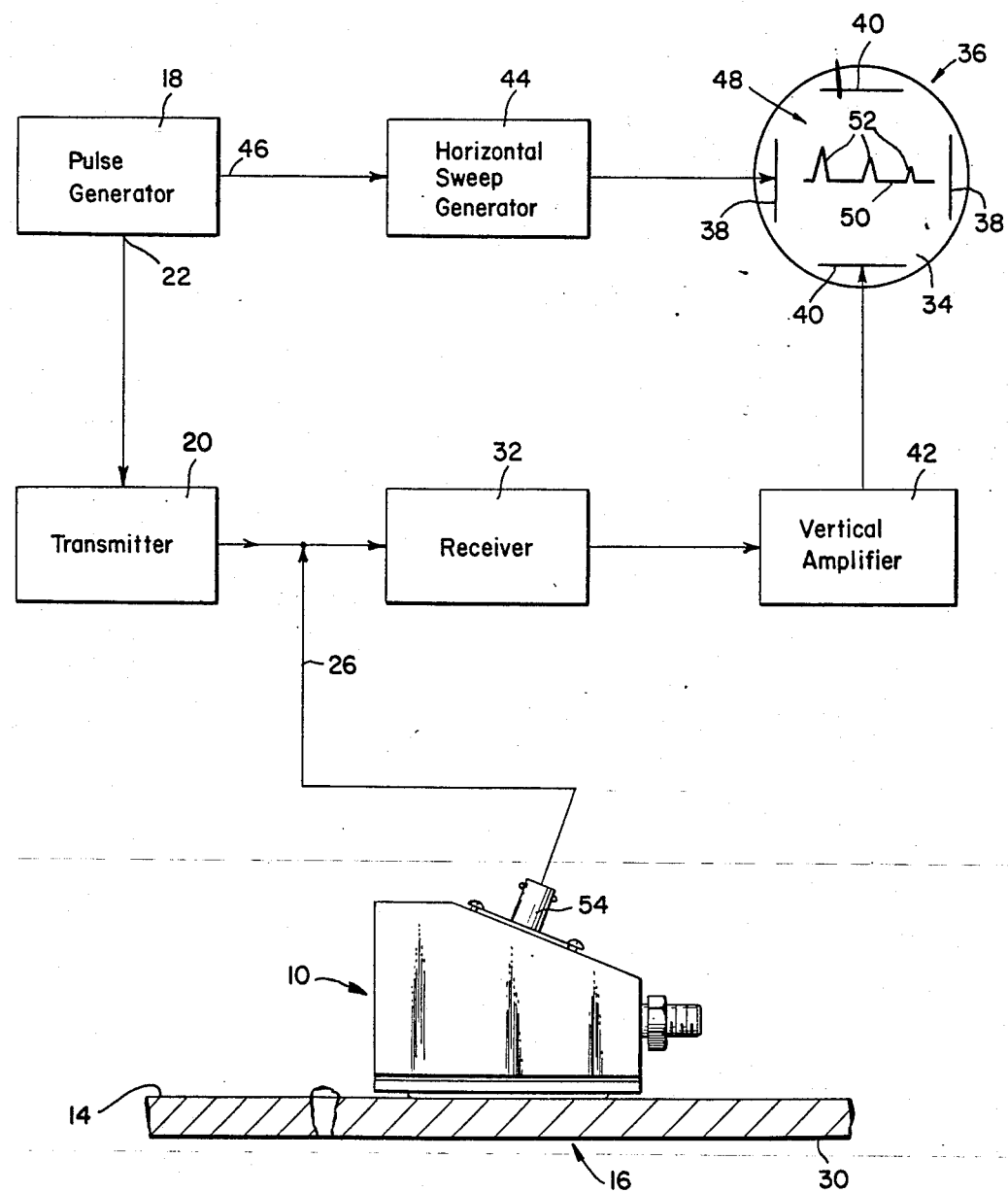
FIG. 1 is a block diagram of a nondestructive testing system utilizing an ultrasonic "sled" embodying one form of the present invention.
Figure 2:
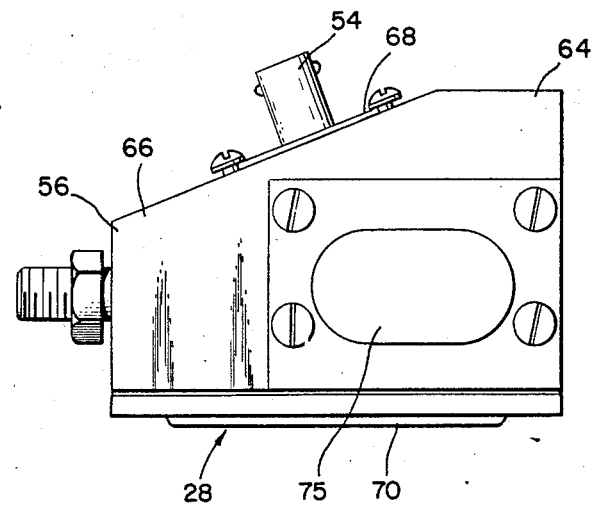
FIG. 2 is a side view, on an enlarged scale, of the sled used in the system of FIG. 1.
Figure 3:
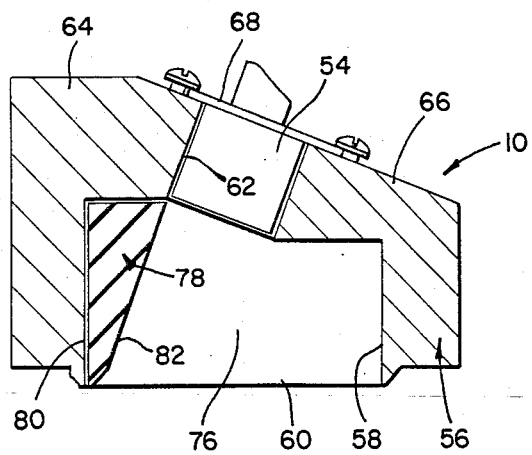
FIG. 3 is a cross-sectional view of the sled taken substantially along the plane of line 3—3 in FIG. 4.
Figure 4:
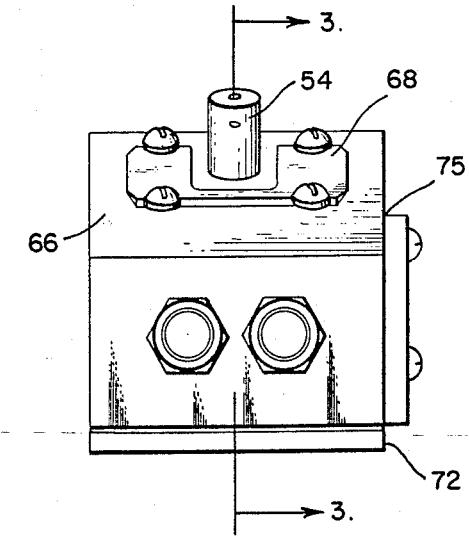
FIG. 4 is an end view of the sled.

Referring to the drawings in more detail, and particularly to FIG. 1, the present invention is particularly adapted to be embodied in an ultrasonic sled 10 for use in an ultrasonic nondestructive testing system 12. The sled 10 is adapted to slide or ride along the surface 14 of a workpiece 16 while being acoustically coupled thereto. The sled 10 is adapted to transmit ultrasonic energy into the workpiece 16 in response to a driving electrical signal. It is also adapted to receive ultrasonic energy from the workpiece 16 and produce received electrical signals corresponding to the incident ultrasonic energy.

Although the sled 10 may be employed in any type of ultrasonic nondestructive testing system (e.g., a continuous wave, pulse echo, through transmission, etc.), in the present instance it is shown as being embodied in a so-called pulse-echo system 12. Moreover, although the sled 10 may function as just a transmitter or just a receiver, in the present instance it is shown functioning as a combined transmitter and receiver. Also in this instance, the sled 10 is arranged to be operated in direct, intimate contact with the surface 14 of the workpiece 16.

A block diagram of a typical ultrasonic pulse-echo nondestructive testing system 12 is shown in FIG. 1. Included therein is the instrumentation for transmitting and/or receiving the electrical signals associated with the sled 10. A clock circuit or pulse generator 18 produces a series of repetitively occurring clock or timing pulses.

The pulse generator 18 is usually a free-running or oscillating device such as multivibrator or the like. A first train of timing pulses is present on a first outlet 22 while a second train of timing pulses is present on the second outlet 46. The pulses in the two trains may occur simultaneously or the pulse in the second outlet may be delayed slightly behind those in the first train.

The timing pulses produced by the pulse generator 18 are effective to determine the repetition rate at which the entire system 12 operates. This repetition rate is not believed to be particularly critical and may vary over a wide range. However, by way of example, it may be in the region of about 1 kilocycle per second.

A pulser or transmitter 20 is coupled to one of the outputs 22 of the pulse generator 18. The transmitter 20 is thereby made responsive to the timing or clock pulses whereby it will operate synchronously therewith. Each time a clock pulse occurs the transmitter 20 produces a pulse suitable for driving the sled 10 and causing it to transmit a pulse of ultrasonic energy.

The driving signal is normally either a high voltage pulse or a burst of rapidly alternating cycles of high peak voltage. The frequency of a single pulse is normally in a range of about 25 kilocycles or less up to about 25 megacycles or higher. Under some circumstances, the driving signal is a pulse which persists for a single cycle or less. However, more commonly, the driving signal includes a burst of a limited number of cycles, for example, 5 to 10 cycles or more.

The output of the transmitter 20 is coupled to the sled 10 for supplying the driving signals thereto. Normally a fairly long flexible, coaxial cable 26 is used. This allows the sled 10 to be separated from the instrumentation and placed on the workpiece 16 wherever it may be and then manually moved around on the surface 14 of the workpiece 16 while the system 12 is operating.

Each time a driving signal occurs it causes a corresponding burst or pulse of ultrasonic energy to be transmitted from the sled 10. The attenuation of ultrasonic energy in air, particularly at the higher frequencies, is very large. It is therefore highly desirable to provide a high degreee of acoustical coupling between the sled 10 and the workpiece 16.

In the so-called contact form of testing, the face 28 of the sled 10 is placed in direct, intimate contact with the surface 14 of the workpiece 16. Hopefully, this eliminates any air between the face 28 and the surface 14. However, generally it is highly desirable to also provide some form of couplant between the workpiece 16 and the sled 10. By way of example, this may be a thin film of water, glycerin, etc.

The ultrasonic energy from the sled 10 is propagated from the face 28 into the workpiece 16. If there are any acoustical discontinuities within the workpiece 16, they act as reflectors whereby echoes of ultrasonic energy are returned to the sled 10. Also ultrasonic energy incident on the front surface 14 and rear surface 30 of the workpiece 16 is reflected back.

Ultrasonic energy returned from the workpiece 16 to the sled 10 causes a corresponding electrical signal to be generated. This electrical signal includes a radio frequency (RF) "carrier" which has the same frequency as the ultrasonic energy. The "envelope" of the carrier wave (i.e., the variations in the amplitude) corresponds to the various echoes which are reflected back to the sled 10.

The electrical, received signal from the sled 10 is coupled back over the coaxial cable 26 into a receiver 32. The receiver 32 is effective to receive or detect the electrical signal. The receiver 32 is usually effective to remove the carrier wave and one side of the modulating envelope from the received signal. This results in a video signal corresponding to one side of the RF signal.

The output or video signal from the receiver 32 is coupled to one or more suitable utilizing or indicating means. Although such means may be any of a wide variety of types, in the present instance, by way of example, an oscilloscope 34 is shown. The oscilloscope includes a cathode ray tube 36 having deflection means such as horizontal and vertical deflection plates 38 and 40, respectively.

The output of the receiver 32 is coupled to a vertical amplifier 42. This amplifier 42 is effective to increase the amplitude of the video signal and to improve the signal-to-noise ratio. The output of the amplifier 42 is coupled to the vertical deflector plates 40 in the cathode ray tube.

A horizontal sweep generator 44 is coupled to the second output 46 of the pulse generator 18 and to the horizontal deflection means or plates 38. As a consequence, each time a clock pulse occurs, the electron beam is swept horizontally across the face of the cathode ray tube 36. If the face 28 of the sled 10 is disposed directly on the workpiece 16, the pulses in the two trains on the two outputs 22 and 46 may occur simultaneously whereby the horizontal sweep across the tube 36 is initiated simultaneously with or very shortly after the transmission of the ultrasonic pulse. Alternately, there may be a predetermined amount of time delay between the pulses in the second train and those in the first train.

The sweep generator 44 produces a sweep signal that varies as a function of the velocity of ultrasonic energy in the workpiece 16. As a result, the horizontal distance across the face of the cathode ray tube 36 corresponds to the distance into the workpiece 16.

Since the output of the vertical deflection amplifier 42 is coupled to the vertical deflection plates 40 in the cathode ray tube 36, the electron beam in the tube 36 is deflected vertically according to the amplitude of the video signal as it is swept longitudinally across the face of the tube 36. This results in a visual display 48 being created on the face of the tube 36.

The display 48 includes a horizontal trace 50 with one or more vertical deflections or marks 52 spaced therealong. The initial marks normally correspond to the original driving signal applied to the sled 10. This is usually followed by a sequence of vertical deflections or marks corresponding to any received signals produced by the sled 10 as a result of any returning echoes.

The horizontal displacements of the vertical marks 52 along the trace 50 correspond to the times of reception of the corresponding echoes and thus are a function of the range or distance to the reflecting targets. The amount of the vertical deflection or vertical heights of the mark is a function of the magnitude of the echo and is therefore a function of the size of the target.

In order to transmit and receive the ultrasonic energy, the sled 10 has a search unit 54 mounted therein. The search unit 54 includes an electroacoustic transducer which is normally a piezoelectric member or crystal having electrodes affixed to the opposite sides thereof. The application of a voltage to the crystal causes it to be physically distorted whereby it will physically vibrate and radiate ultrasonic energy. Conversely, the physical distortion of the crystal will generate a corresponding electrical signal.

The sled 10 includes a housing 56. The housing 56 may be fabricated from any suitable material, but it has been found that a strong rigid material is well suited for this purpose. The housing has a generally rectangular shape. However, for reasons explained in more detail subsequently, a portion 66 of the top 64 of the housing 56 may be cut at an oblique angle. This angle corresponds to the angle of incidence of the beam of ultrasonic energy on the surface 14 of the workpiece 16.

A cavity or chamber 58 is formed into the housing 56. This cavity or chamber 58 may be formed by die casting the housing 56 and/or machining the cavity 58, etc. In the present instance the cavity 58 has generally a rectangular shape similar to that of the housing 56. The cavity 58 extends upwardly from the face 28 of the sled 10. As a result, it forms an enlarged rectangular opening 60 in the face 28.

In addition, an opening or passage 62 is provided. This passage 62 is normally drilled inwardly through the inclined side 66 or the top of the housing 56 so as to open into the cavity 58. The search unit 54 is inserted through this opening 62 whereby the active face thereof is positioned in the cavity 58. The search unit 54 can be of a more or less standard design having a cylindrical shape corresponding to the shape of the passage 62. A mounting plate 68 is fastened onto the inclined side 64 and clamps the search unit 54 in position.

One end of the coaxial cable 26 is attached to the rear of the search unit 54. The opposite end is coupled to the transmitter 20 and the receiver 32 in the system 12.

The face 28 of the sled 10 is adapted to fit onto and slide along the surface 14 of the workpiece 16. A diaphragm 70 or similar member is attached to the face 28 of the sled 10. The present diaphragn 70 is a pliable member that is stretched over the opening 60. A face plate or frame 72 is attached to the housing 56.

The frame 72 has a generally rectangular configuration which corresponds to the periphery of the opening 60 formed by the cavity 58. The periphery of the diaphragm 70 is clamped in position on the housing 56 by this frame 72. As a result, the center portion of the diaphragm 70 is stretched over the opening 60 whereby it closes the opening 60 into the cavity 58.

The diaphragm 70 is flexible and resilient so that it "bulges outwardly" beyond the frame 72. This allows the diaphragm 70 to be in direct intimate contact with the surface 14 of the workpiece 16.

Under some circumstances, it may be desirable to provide spacers or guide bars 74 on the face 28 of the sled 10. In the present invention, a pair of guide bars 74 are included. The guide bars 74 are relatively thin members (i.e., about the amount the diaphragm projects beyond the frame 72). The guide bars 72 have a width which is about equal to the width of the sides of the frame 72. The guide bars 74 are secured in position by a plurality of screws 71 that can be threaded into the openings 73.

Figure 5:
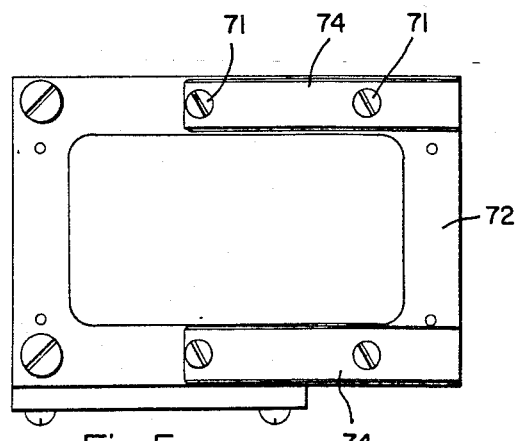
FIG. 5 is a bottom plan view of the sled with a set of guide bars thereon arranged in a first configuration.
Figure 6:
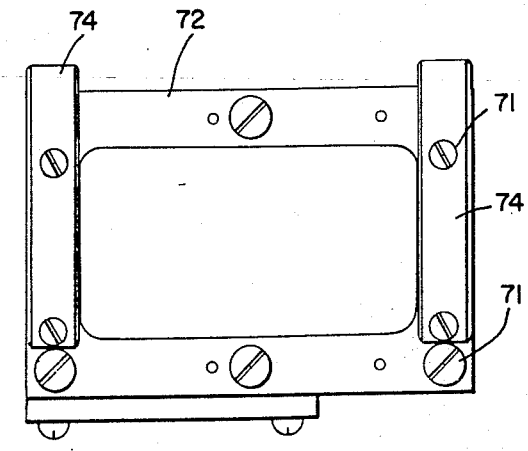
FIG. 6 is a bottom plan view similar to FIG. 5 but showing the set of guide bars arranged in a second configuration.

As seen in FIG. 5, these guide bars 74 may be positioned longitudinally. Alternately, as seen in FIG. 6, they may be positioned transversely. The guide bars 74 are adapted to engage and ride along the surface 14 of the workpiece 16. The guide bars 74 support the sled 10 in a predetermined position and regulate the amount of pressure and the area of contact between the diaphragm 70 and the surface 14.

The interior of the cavity 58 is filled with a suitable acoustical couplant 76. This couplant 76 is effective to couple the ultrasonic energy transmitted from the search unit 54 through the cavity 58 to the diaphragm 70 and conversely to return the ultrasonic energy from the diaphragm 70 to the search unit 54. As a result, the energy can be effectively coupled between the search unit 54 and the workpiece 16.

A wide variety of couplants may be employed. However, the couplant 76 preferably is capable of completely filling the cavity 58 and of readily flowing around therein to accommodate movements of the diaphragm 70. In addition, a diaphragm 75 may be secured in position over an opening in the side of the housing 56. This diaphragm 75 is effective to accommodate the movement of the liquid couplant.

The acoustical properties of the couplant 76 (i.e., the impedance, etc.) should correspond to those of the search unit 54 and the workpiece 16. It has been found that numerous liquids are well suited for this purpose. By way of example, the present couplant 76 is water. However, glycerin and similar materials may be used.

There is a tendency for some of the ultrasonic energy transmitted from the search unit 54 into the cavity or chamber 58 to reflect from various interfaces present in cavity 58. These reflections can eventually reach the search unit 54 whereby spurious signals are generated by the search unit 54. Also, some of the energy which is coupled through the diaphragm into the cavity 58 can be reflected in a similar manner.

When the ultrasonic energy is incident upon the search unit 54, it creates spurious electrical signals. These signals are received by the receiver 32 and fed to the cathode ray tube 36. This in turn results in spurious indications being produced in the display 48. These indications can obscure the valid markers 52 or at least make reading the display 48 very difficult.

In order to prevent the spurious reflections and the resultant signals, one or more suitable acoustical dampening blocks 78 may be mounted in the cavity 58. In the present instance, an acoustical dampening member 78 is permanently mounted on one of the side-walls 80 of the cavity 58. The surface 82 of the dampening block 78 forms an interface between the block 78 and the couplant 76. Preferably this interface is disposed substantially parallel to but outside of the beam of ultrasonic energy transmitted by the search unit 54. As a result, the principal or useful portion of the energy will not be incident on the interface. Instead, it will propagate directly to the diaphragm 70 and into the workpiece 16. However, any spurious energy will be incident upon the interface. This energy is coupled into the block 78 and absorbed.

It has been found preferably for the dampening block 78 to be of a material having acoustical impedance closely resembling those of the couplant 76. This is particularly true of the acoustical impedances. If there is a close matching of impedances, there will be very little, if any, of the energy reflected from the interface. Under these circumstances, if any energy is incident upon the interface, substantially all of it is coupled into the block 78 and very little is reflected back.

It has also been found desirable for the dampening block 78 to have a large amount of acoustical attenuation. The acoustical energy coupled into the block 78 is absorbed within the material. If the block 78 does not have a large attenuation, some of the energy will be reflected from the backside 80 of the block 78 and returned to the liquid couplant 76 in the cavity 58.

There are a wide variety of materials suitable for use in the dampening block 78. However, it has been found that various types of elastomers, rubber, etc., are particularly adapted for this use. By way of example, where the couplant 76 is water, as in the present instance, various urethanes have the desired properties.

In particular, it has been found that Adiprene has acoustical impedance that is very close to that of water. As a consequence, when there is an interface between the Adiprene and water, there is little or no reflection of any of the ultrasonic energy incident on the interface.

Also, Adiprene has a relatively high attenuation loss. As a consequence, substantially all of the energy which enters the Adiprene is absorbed therein and little or no energy is returned. It can be seen that if there is a low attenuation loss, the energy which propagates through the block 78 to the interface 80 between the block 78 and the backing of the housing will cause a reflection. However, since the energy is absorbed within the block 78 there will be no such reflections. As a consequence, all of the spurious energy in the liquid couplant 76 will be absorbed and dissipated and not coupled to the search unit.

Although only a single embodiment of the invention is disclosed herein, it will be readily apparent to persons skilled in the art numerous changes and modifications may be made thereto without departing from the spirit of the invention. For example, there may be a plurality of transducers in a common housing with a separate dampening member for each of the transducers. Accordingly, the present disclosure is for illustrative purposes only and does not limit the invention which is defined only by the following claims.

What is claimed is:
1. A device for non-destructively inspecting a workpiece contacted by said device comprising:
  a housing having a face on one side thereof for scanning a workpiece,
  a chamber in said housing forming an opening in said face,
  a diaphragm on said face closing the opening therein,
  ultrasonic search unit means mounted on said housing for transmitting and/or receiving a beam of ultrasonic energy, said search unit extending into said chamber,
  a liquid acoustical couplant entirely self-contained within said chamber acoustically coupling the search unit to the diaphragm,
  an acoustical dampening member having a high acoustical attenuation and acoustical properties matching those of the couplant, said dampening member being mounted in said chamber out of alignment with said search unit with a surface thereof forming an interface between the dampening member and said couplant, said surface being disposed substantially parallel to and immediately adjacent to but outside of the beam of ultrasonic energy transmitted and/or received by said search unit and at an angle with respect to signals reflected off of a workpiece contacted by said diaphragm passing perpendicularly through said diaphragm; and
  means for mounting said search unit means to direct ultrasonic energy toward said diaphragm at a significant angle away from the perpendicular to cause ultrasonic energy reflected directly from the surface of a test object in engagement with said diaphragm to impinge upon and be absorbed by said acoustic dampening member.

2. A sled for ultrasonically nondestructively inspecting a workpiece, said sled including the combination of:
  a housing having a face on one side thereof for scanning along the surface of the workpiece,
  a chamber in said housing forming an opening in said face,
  a diaphragm on the face closing the opening and sealing the chambker, said diaphragm being flexible and resilient and bulging out from said chamber;
  guide means secured to said sled for spacing said sled to slide along the surface of the workpiece, with said diaphragm in direct intimate engagement with said workpiece;
  an ultrasonic search unit adapted to transmit and/or receive ultrasonic energy along a predetermined beam pattern, said ultrasonic search unit being mounted on said housing and extending into said chamber with said beam pattern aimed at said diaphragm,
  a liquid acoustical couplant filling said chamber and self-contained therein and acoustically coupling the search unit to the diaphragm,
  an acoustical dampening member, said member being mounted on said housing inside said chamber with a surface of said member forming an interface with said couplant, said member having acoustical properties matching the acoustical properties of the couplant and a large attenuation and said surface being disposed substantially parallel to but outside of the beam of ultrasonic energy transmitted and/or received by said search unit and at an angle with respect to signals reflected off of a workpiece contacted by said diaphragm passing perpendicularly through said diaphragm, and
  means sealed to said chamber for accommodating movement of said liquid couplant, said means being located on a surface of said housing other than said scanning face.

3. The device of claim 1 wherein said dampening member is an elastomer.

4. The device of claim 1 wherein said dampening member is a block of urethane.

5. The device of claim 4 wherein said urethane block is Adiprene.

6. The combination of claim 2 wherein said member is a urethane elastomer.

7. The combination of claim 6 wherein said urethane elastomer is Adiprene.

* * * * *